United States Patent [19]

Galen

[11] Patent Number: 4,584,887
[45] Date of Patent: Apr. 29, 1986

[54] SOLID SORBENT AIR SAMPLER

[75] Inventor: Theodore J. Galen, Friendswood, Tex.

[73] Assignee: The United States of America as represented by the Administrator of the National Aeronautics & Space Administration, Washington, D.C.

[21] Appl. No.: 659,474

[22] Filed: Oct. 10, 1984

[51] Int. Cl.[4] ............................................. G01N 1/24
[52] U.S. Cl. .............................. 73/863.31; 73/863.21; 73/864.34; 73/863.72
[58] Field of Search ........... 73/863.31, 863.21, 863.73, 73/864.71, 864.34, 864.81, 864.85, 863.22, 863.23, 864.35, 863.86, 863.83, 863.84, 863.72

[56] References Cited

U.S. PATENT DOCUMENTS

| | | | |
|---|---|---|---|
| 1,873,010 | 8/1932 | Mitton | 73/864.35 |
| 3,080,759 | 3/1963 | McQuaid | 73/863.73 |
| 3,114,393 | 12/1963 | Vlasic | 73/863.73 X |
| 3,401,564 | 9/1968 | Hrdina | 73/864.85 X |
| 3,540,261 | 11/1970 | Scroggins | 73/28 |
| 3,731,531 | 5/1973 | Brittan et al. | 73/863.31 X |
| 3,765,247 | 10/1973 | Riggs | 73/863.23 |
| 3,901,084 | 8/1975 | Brailsford | 73/864.35 |
| 3,953,152 | 4/1976 | Sipin | 73/863.21 X |
| 3,978,732 | 9/1976 | Dillman | 73/863.31 X |
| 3,978,888 | 9/1976 | Naono | 73/863.31 X |
| 4,080,832 | 3/1978 | Moody et al. | 73/863.23 |
| 4,091,674 | 5/1978 | Amey | 73/864.34 |
| 4,120,202 | 10/1978 | Range et al. | 73/864.34 |

OTHER PUBLICATIONS

"A Continuous Sequential Air Sampler in Environmental Studies", *Indian Journal of Technology*; vol. 11, No. 50, pp. 230-232; May 1973; P. Zutchi et al.

*Primary Examiner*—Stewart J. Levy
*Assistant Examiner*—Tom Noland
*Attorney, Agent, or Firm*—Russell E. Schlorff; John R. Manning; Marvin F. Matthews

[57] ABSTRACT

A fluid sampler for collecting a plurality of discrete samples over separate time intervals. The sampler comprises a sample assembly having an inlet and a plurality of discreet sample tubes each of which has inlet and outlet sides. A multiport dual acting valve is provided in the sampler in order to sequentially pass air from the sample inlet into the selected sample tubes. The sample tubes extend longitudinally of the housing and are located about the outer periphery thereof so that upon removal of an enclosure cover, they are readily accessible for operation of the sampler in an analysis mode.

7 Claims, 3 Drawing Figures

SOLID SORBENT AIR SAMPLER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

This invention relates to portable fluid samplers, and more particularly, to self contained portable air sampling devices suitable for the detection of trace amounts of contaminate gases over a plurality of discreet sampling intervals.

BACKGROUND ART

There are various environments in which self contained portable fluid samplers are useful. For example, it is often desirable to monitor ambient air for contaminants and to obtain samples which enable the detection of even minute quantities of such contaminants. Such devices should be relatively small and lightweight so that they can be readily transported from one location to another. They are useful in industrial applications such as in chemical plants and the like where workers face a potential exposure to airborne toxic substances over prolonged periods of time. Another environment in which portable samplers may be employed is in mining operations. Yet a further use of such samplers is in space-craft programs where it is desirable to collect composite samples over periods of time in order to determine the exposure of the crew to contaminants within the space-craft cabin.

One type of portable air sampling monitor is disclosed in U.S. Pat. No. 4,080,832 to Moody et al. In the monitor disclosed in this patent, a bellows is provided which is collapsed and expanded by a motor under the control of a clock pulse circuit. Each time the bellows is expanded, it acts as a suction pump to draw air in through a filter. The clock pulse circuit is programmed to operate the bellows at a desired frequency, e.g., once every minute, during a desired interval of time such as the workshift of an industrial worker. The logic circuitry associated with the air sampler counts the number of times the bellows is pulsed during the sampling interval so that the total air volume flowing through the air filter can be calculated. At the end of the sampling interval, the filter is removed and analyzed to determine the identity and quantity of the material trapped in the filter. From this and from the logic circuit parameters, the contaminate concentration in the air can be determined.

U.S. Pat. No. 4,091,674 to Amey discloses an air sampling pump for use in air monitoring systems. In this reference, the pump is disclosed as a bellows-type suction pump mounted on the exhaust side of a collector tube so that the pump operates to pull sample air through the tube. Means are provided in Amey to carefully monitor the operation of the pump so that air flow through the sample tube can be accurately measured.

Yet another air sampling device is disclosed in U.S. Pat. No. 3,540,261 to Scoggins. In Scoggins, a circular magazine is mounted within a cylindrical housing for rotation about the axis of the housing. The housing is provided with a sampling port in the cylindrical wall thereof. A plurality of samplers are mounted around the periphery of the magazine in a uniformly spaced relationship. The magazine is then rotated to bring each of the samplers into engagement with the air monitoring port for desired collection periods which can range from five minutes up to twenty-four hours. Each sampler includes a sampling medium secured within a housing. A vacuum conduit or passage extends rearwardly through the housing so that upon exposure of the sampler to the atmosphere through the sampling port, air can be drawn in by means of a suitable vacuum source.

DISCLOSURE OF THE INVENTION

In accordance with the present invention, there is provided a new and improved fluid sampler of the type adapted for use with volatile trapping means such as solid sorbents and which is totally self contained and enables the collection of a plurality of discreet samples over separate time intervals. The collected samples are not exposed to cross contamination and are subject to laboratory analysis without undue handling leading to external contamination.

The self contained portable fluid sampler of the present invention comprises a sample assembly and a detachable flow assembly. The sample assembly includes fluid inlet means and fluid outlet means and a plurality of sample tubes containing volatile trapping means. Means are provided for selectively directing flow from the inlet means to one of the sample tubes and from the sample tube to the outlet means. The detachable flow assembly functions to move fluid through the sample assembly. Coupling means are provided for connecting and disconnecting the flow assembly whereby the flow assembly can be disconnected from the sample assembly and the sample assembly used in reverse flow relation for analysis of volatiles trapped in said sample tubes.

In a further aspect of the invention, there is provided a sampler comprising a sample assembly having a sample inlet and a sample outlet and a plurality of discreet sample tubes. Each sample tube has inlet and outlet sides. The sampler includes valve means for isolating each of the sample tubes. The valve means functions to place the inlet and outlet sides of the isolated tube in fluid communication with the sampler inlet and outlet means. Pump means are provided for passing fluid through the inlet port, the isolated sample tube at a designated flow rate and then exhausting the fluid. In the preferred embodiment of the invention disclosed herein, the sample tubes extend longitudinally of the sample assembly and are mounted about the outer periphery of a supporting frame. The valve means and the pump means are located interiorly of said tubes at longitudinally spaced locations. This arrangement enables the attainment of all of the essential elements of the sampler in a relatively compact structure. In addition, the pump means and associated flow assembly components can be withdrawn and the sampler assembly can be retained as a unit and subject to an elution process in which the sample tubes are heated during desorption of the contaminates from the tubes by a suitable heater and transported by a suitable eluting gas to a chromatograph.

BRIEF DESCRIPTION OF THE DRAWINGS

FIG. 1 is a an exploded perspective view with parts broken away of a sampler emboding the present invention.

DETAILED DESCRIPTION

Figure 1:
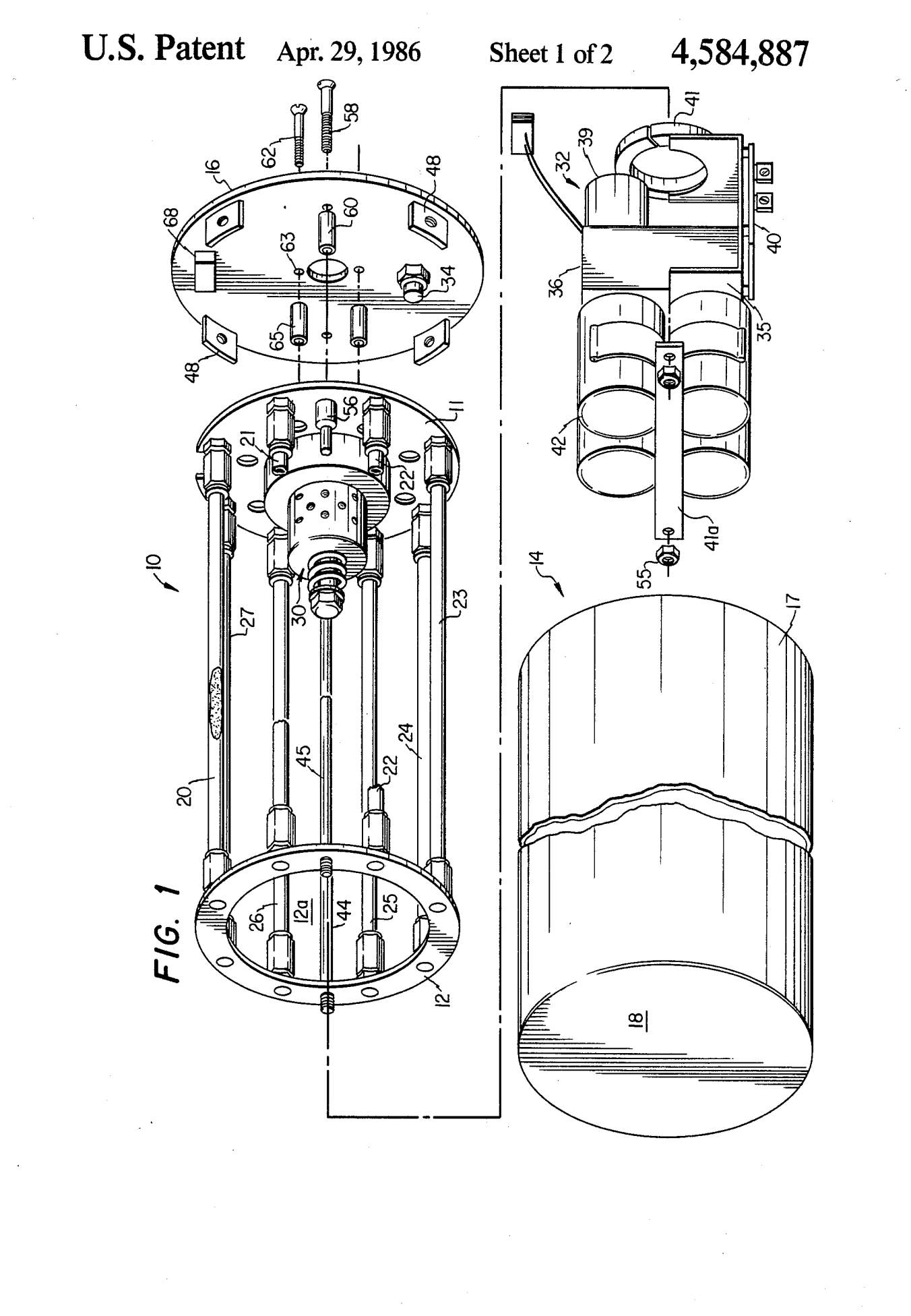
Figure 3:
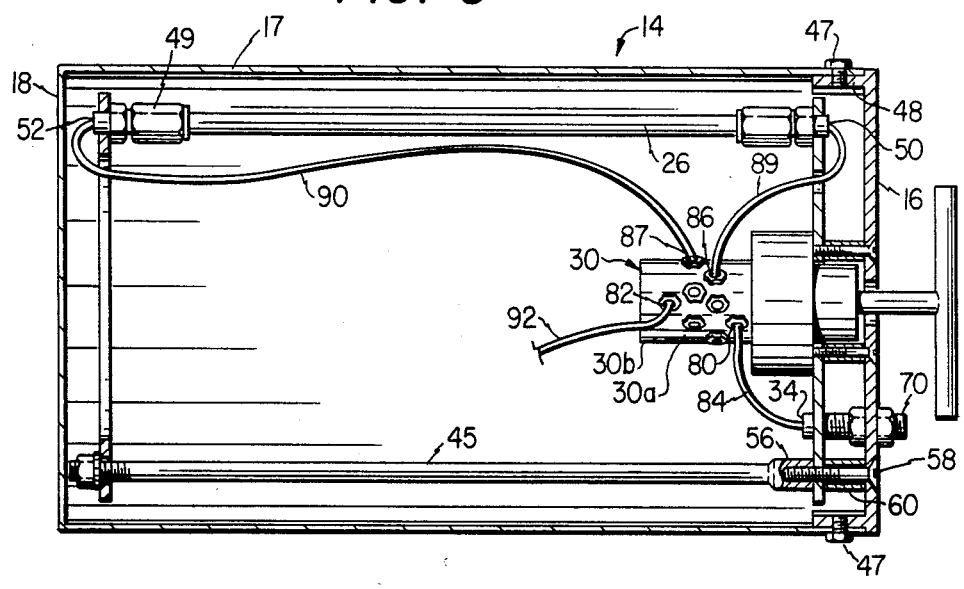
FIG. 3 is a side view, partly in section, of the sampler with parts broken away and parts shown in rotated relation.

As shown in the drawings, the sampler of the present invention includes a sample assembly having an elongated cylindrical frame 10 comprising front and rear mounting rings 11 and 12, and a cylindrical, cup-shaped cover 14, shown in its entirety in FIGS. 1 and 3. The cover fits on a front plate 16 and includes a removable cylindrical cover tube 17 and rear cover plate 18. Mounted on the sample assembly frame are a plurality of discreet sample tubes 20 through 27, each having inlet and outlet sides. The sample assembly includes a valve 30 which functions to isolate each of the sample tubes and place the inlet and outlet sides thereof in fluid communication with the sampler inlet and exhaust. The sample tubes are arranged about the periphery of the frame and the valve 30 and an associated flow assembly 32 are located interiorly within the tubes at longitudinally spaced locations along the housing. With an individual sample tube isolated, the flow assembly functions to draw air into the sampler through an inlet port 34, pass the air sample through the selected sample tube and thence exhaust the air to the atmosphere.

Figure 2:
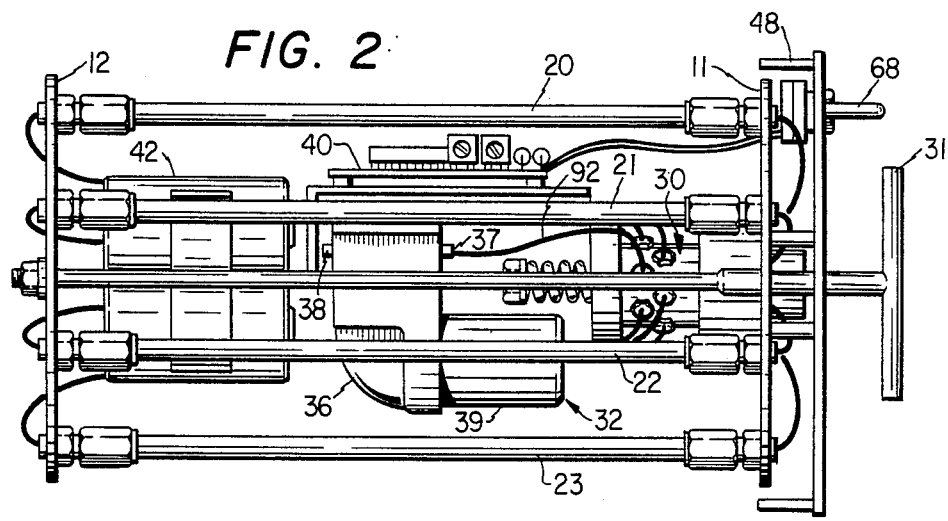
FIG. 2 is a side view of the sampler illustrating the pump and electronic module in place.

Referring to FIGS. 1 and 2 of the drawing, the sample tubes 20-27 extend between the front mounting ring 11 and the rear mounting ring 12. The rear mounting ring 12 defines an enlarged opening 12a through which the detachable flow assembly 32 is inserted. The flow assembly 32 includes a mounting bracket 35 and a positive displacement pump 36 having inlet and exhaust sides 37 and 38, respectively. An electronics module 40 and a power pack 42 are secured to the mounting bracket. The pump is a constant rate positive displacement pump driven by a DC motor 39 within the pump housing. A suitable pump including the DC motor is available from Wisa Precision Pumps Bayonne, N.J. identified as Romega #10. The electronics module includes a DC timing circuit which provides a variable frequency pulse output to drive the pump. For example, the timing circuit output frequency may range from a continuous signal to a frequency of 1 pulse every 7 seconds. An on/off switch 68 connects the power pack to the pump and to the electronics module. The front mounting ring 11 supports valve 30. Valve 30 is a double action multiport valve which functions to sequentially connect each tube individually in series between the sampler inlet and the sampler exhaust.

The mounting bracket 35 of the flow assembly includes a split collar 41 which is adapted to fit over the end 30b of the valve body 30a. Collar 41 may be secured to the end of the valve body by any suitable means. For example, as illustrated in FIG. 1 collar 41 may be of a split-ring configuration equipped with fastening means such as a screw (not shown) which may be employed to tighten the collar about the outer surface of the valve body to hold the flow assembly in place. The mounting bracket is also provided with a rear brace 41a which fits over the threaded ends of the stress rods described below.

As best shown in FIGS. 1 and 3, the mounting rings 11 and 12 which hold the sample tubes are in turn secured together by stress rods 44 and 45. The front plate 16 is secured to the valve mounting ring 11 in a spaced relationship. The integrally formed closure tube 17 and rear closure plate 18 are secured to the front enclosure cover by means of screws 47 which fit through the cover tube and into tapped holes within tabs 48 extending rearwardly from the front plate.

As exemplified by tube 26 shown in FIG. 3, the ends of the sample tubes are provided with reducing union fittings 49 which are provided at their ends with cylindrical projections. These projections fit into correponding holes in the front and rear mounting rings. Thus, as shown in FIG. 3, the hexagonal fittings at the ends of tube 26 terminate in cylindrical projections 50 and 52 which fit into corresponding holes in rings 11 and 12 respectively. The stress rods are then connected between plates 11 and 12 to hold the plates together with the stress rods carrying longitudinal tensil stress and the sample tubes longitudinal compressive stress. As best shown in FIG. 3, and as exemplified by stress rod 45, the stress rod has external threads at its rear end which fit into a tapped hole in the rear mounting ring. The threaded rear ends of the stress rods also support brace 41a of the mounting bracket. Brace 41a is held in place by nuts 55 (FIG. 1). The front of the stress rod 45 has an enlarged box joint 56 which is internally threaded to receive a screw 58. Screw 58 extends through the front plate 16 and a spacer 60 to secure the front plate to the mounting ring and stress-rod assembly as shown in FIG. 3. As shown in FIG. 1, a somewhat similar arrangement is employed to hold the valve 30 in place. Thus, the valve housing includes 2 tapped holes (not shown) into which screws 62 extend through perforations 63 in the front plate and spacers 65 and into the valve housing. The front plate 16 also supports the on/off switch 68 and a union joint 70 which forms part of the air inlet for the sampler.

The sample tubes preferably are fused glass-lined metal tubes containing volatile trapping means such as a sorbent material which functions to adsorb contaminate materials from an air sample as it is passed through the tube. Preferably, the sorbent material preferentially adsorbs organic compounds from the air sample while permitting inorganic compounds to pass through the sample tube substantially unimpeded. A suitable adsorbent material for use in the present invention is a porous polymer of 2,6-diphenyl-p-phenylene oxide which is available from Altech Associates Houston, Tex. under the trademark "Tenax-GC". This material will function to preferentially adsorb volatile organic compounds which may be present in the air sample e.g. benzene, phenol, ethanol, acetone, formaldehyde hexane, ethyl mercaptan, and ethyl acetate, while allowing the inorganic compounds present in the air to pass through the sample tube in a relatively unadsorbed manner. Specifically, the Tenax-GC polymer will not adsorb oxygen, nitrogen, argon, carbon monoxide, and carbon dioxide and will adsorb water vapor only to a minor extent.

The use of fused glass-lined tubes provides an inert surface which is stable to reactive compounds that may be present in the atmosphere being sampled. A desirable analysis technique involves the use of an analytical system which includes a gas chromatograph with the inlet to the chromatograph equipped with a cryogenic trap to sharpen the chromatographic peaks. The presence of water in the sampling system, which is subject to being desorbed during elution of the samples from the adsorbent, is undesirable since it may freeze at the cryogenic trap to plug the flow to the chromatograph. The glass-lined tubes eliminate the water vapor problem which would be attendant to the use of other materials such as stainless steel.

The valve employed in the present invention is a double action multiport valve having a master inlet port 80, a master outlet port 82, and a plurality of selection ports which are indexed together and associated with the respective master ports. Specifically, in the embodiment illustrated, the valve is an 18 port valve having 8 selection ports associated with the common inlet port 80 and 8 selection ports associated with the common outlet port 82. Each pair of selection ports functions as a set of sample ports associated with a given sample tube. As shown, the valve 30 is equipped with a manual handle 31 connected to an internal valve member (not shown) which functions to selectively direct flow from the inlet port 80 to one of a selected pair of sample ports and from the other of the selected pair to the outlet port 82. It will be recognized, however, that the valve may also be operated electronically under the control of a suitable timing circuit.

The valve 30 with exemplary fluid connections is best illustrated in FIG. 3. As shown the common inlet port 80 on the outer valve body 30a of the valve is connected to the sampler inlet 34 by means of an air line such as a 1/32" O.D. stainless steel tube 84. The tube is connected to the sampler inlet 34 by means of a coupling which includes a filter to prevent particulate material from entering the system. For example, the filter may be a four millimeter filter having a filter size of 0.2 microns. As shown in FIG. 3, the ends of sample tube 26 are connected to inlet selection port 86 and outlet selection port 87 by means of 1/32" stainless steel tubings 89 and 90, respectively. An outlet gas flow line 92 extends from the common outlet port 82 of the valve to the suction side 37 of the pump (See FIG. 2). It will be recognized that each set of selection ports of the valve 30 are similarly connected to one of the sample tubes so that each tube can be sequentially placed in the sampling stream for a desired period of time. Each set of inlet and outlet selection ports are completely isolated from the remaining sets of selection ports in order to avoid contamination from one sample tube to the next. A suitable valve for use in the invention is identified as Part No. NST-8T available from Valco Instruments Houston, Tex.

As noted previously, it is preferred to employ sample tubes which are fabricated from stainless steel with fused glass liners. Glass-lined tubes suitable for use in the invention are available from Scientific Glass Engineering, Inc., Austin, Tex. under the designation GLT. Suitable tubes have a outer diameter of ¼", an internal diameter of 4 mm. and a length of 15 cm. The tubes may be secured at their ends to 1/32" O.D. stainless steel tubing, as described previously, through the use of external-internal reducing unions which employ gas tight compression fittings. Suitable ¼"-1/32" reducing unions (including nuts and ferrules) are available from Valco Instruments Company, Inc., Houston, Tex. designated as Part No. ECEF. The metal-to-metal seals provided by the compression fittings eliminates the need for rubber packings such as o-rings which may cause off-gasing problems.

After operating the sampler in the sample taking mode, the cover assembly 14 is removed from the remainder of the sampler in order to prepare the sampler for operation in the analytical analysis mode. The flow assembly, including the battery pack, pump and electronics module, is then removed from the back of the sampler and the exhaust line 92 is connected to a source of eluting gas. Any suitable eluting gas such as helium may be used. The inlet line 84 through port 34 is connected to a suitable analytical instrument such as a gas chromatograph equipped with a flame ionization detector. The eluting gas is then passed in reverse flow in relation to flow during the sampling mode through each of the sample tubes to desorb contaminants from the polymer and carry them into the chromatograph. It will be recognized that during this mode of operation, each sample tube remains isolated from the others similarly as when operated in the sampling mode. During the desorption step, it usually will be desirable to heat the sample tube in order to promote desorption from the polymer matrix. This is conveniently accomplished in the present invention simply by clamping a heating jacket (not shown) around the tube undergoing desorption. Thus, it will be recognized that the peripheral location of the sample tubes, in addition to enabling the sampler to be constructed in a compact manner, also greatly facilitates operation of the sampler during the analytical analysis mode.

Having described specific embodiments of the present invention, it will be understood that modifications thereof may be suggested to those skilled in the art, and it is intended to cover all such modifications as fall within the scope of the appended claims.

I claim:
1. A self contained portable fluid sampler comprising:
   a. a sample assembly formed of a fluid inlet means; a plurality of sample tubes containing volatile trapping means; a supporting framework for mounting the sample tubes, the sample tubes being mounted longitudinally about the periphery of the framework, a first end of the framework being open providing access to the interior of the framework, a second end of the framework having the fluid inlet means and a multiport valve mounted therein; the multiport valve having an inlet port, a plurality of pairs of sample ports, an outlet port, and a valve member for selectively directing flow from the inlet port to one of a selected pair of sample ports and from the other of the selected pair of sample ports to the outlet port; fluid means connecting the fluid inlet to the inlet port of the multiport valve; and fluid means connecting the sample ports of the multiport valve to one of the sample tubes; the sample port from the inlet side of the multiport valve being connected to the sample tube at the second end of the framework whereby the transit from the inlet of the system to the sample tube is relatively short, the flow path for the sample being formed of non-reactive metallic material whereby contamination is eliminated; and
   b. a detachable flow assembly for moving fluid through the sample assembly insertable through the first end of the framework for location interiorly of the periphery containing said sample tubes, said flow assembly including a pump; means for energizing said pump, and coupling means for connecting and disconnecting the pump of the flow assembly to the outlet of the multiport valve, whereby the flow assembly can be disconnected from the sample assembly and withdrawn from the fluid sampler and the sample assembly used in reverse flow relation for analysis of volatiles trapped in said sample tubes.
2. The fluid sampler of claim 1 wherein the sample tubes are stainless steel with a fused glass lining.

3. The fluid sampler of claim 1 wherein a cylindrical frame is formed of a pair of annular rings, each ring having a plurality of spaced openings interiorly of its periphery, the openings of one ring mating with the openings of the other ring the sample tubes having reducing unions on their ends with the ends of the reducing unions being cylindrical to fit in a mating pair of openings, a pair of threaded members, being placed in diametrically opposite pairs of the spaced openings, the threaded members being tightened to provide tension with the sample tubes responding in compression.

4. The fluid sampler of claim 1 including a cylindrical cup-shaped cover which surrounds said sample tubes and is removeable to expose said sample assembly and flow assembly.

5. The fluid sampler of claim 1 wherein said sample tubes contain a sorbent material which functions to selectively adsorb organic compounds from said fluid while permitting inorganic compounds in said fluid to pass through said sample tubes without substantial adsorption.

6. The fluid sampler of claim 1 wherein said pump comprises a constant rate pump and timing means for supplying a pulsed source of driving power to said pump for varying the pulse frequency of said driving power.

7. The fluid sampler of claim 6 wherein said pump means comprises a positive displacement pump located in fluid communication with said valve outlet whereby said pump acts as a suction pump to draw air through said inlet and said sample tube.

* * * * *